(12) United States Patent
Panagotacos et al.

(10) Patent No.: US 7,344,280 B2
(45) Date of Patent: *Mar. 18, 2008

(54) ILLUMINATOR ASSEMBLY

(75) Inventors: George W. Panagotacos, Corona, CA (US); David G. Pelka, Los Angeles, CA (US); Roland Winston, Merced, CA (US)

(73) Assignee: Teledyne Lighting and Display Products, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/633,305

(22) Filed: Dec. 4, 2006

(65) Prior Publication Data

US 2007/0086197 A1   Apr. 19, 2007

Related U.S. Application Data

(63) Continuation of application No. 10/675,504, filed on Sep. 30, 2003, now Pat. No. 7,163,318.

(60) Provisional application No. 60/414,443, filed on Sep. 30, 2002.

(51) Int. Cl.
*F21V 29/00*   (2006.01)
(52) U.S. Cl. .................. 362/294; 362/580; 362/800
(58) Field of Classification Search ............... 362/294, 362/547, 455, 555, 580, 267, 800; 257/100
See application file for complete search history.

(56) References Cited

U.S. PATENT DOCUMENTS

| | | | |
|---|---|---|---|
| 4,271,408 A | 6/1981 | Techima et al. | |
| 5,310,344 A | 5/1994 | Vassiliadis et al. | |
| 5,401,171 A | 3/1995 | Paghdiwala | |
| 5,485,317 A | * 1/1996 | Perissinotto et al. | ........ 359/712 |
| 5,616,141 A | 4/1997 | Cipolla | |

(Continued)

FOREIGN PATENT DOCUMENTS

GB   2329756 A   3/1999

(Continued)

OTHER PUBLICATIONS

*Compact Nonimaging Lens with Totally Internally Reflecting Facets*, Parkyn, et al., Journal: Proc. SPIE vol. 1528, p. 70-81, Nonimaging Optics: Maximum Efficiency Light Transfer, Winston, et al., Eds. (SPIE Homepage); Publication Date: Oct. 1991.

(Continued)

*Primary Examiner*—Sandra O'Shea
*Assistant Examiner*—Gunyoung T. Lee
(74) *Attorney, Agent, or Firm*—Kirkpatrick & Lockhart Preston Gates Ellis LLP

(57) ABSTRACT

An apparatus includes a lens having a light entrance end forming a recess defining a concave surface, a heat sink having an end portion facing the recess and a light source positioned to transmit light having a predetermined wavelength via the concave surface of the recess into the lens. The lens may be a non-imaging lens or a total internal reflection lens (TIR) configured to radiate optical radiation received at the concave surface. The light source is in thermal communication with the heat sink to conduct heat generated by the light source to the heat sink.

35 Claims, 12 Drawing Sheets

U.S. PATENT DOCUMENTS

| | | | |
|---|---|---|---|
| 5,752,833 A | 5/1998 | Yamamoto | |
| 5,775,792 A | 7/1998 | Wiese | |
| 6,077,073 A | 6/2000 | Jacob | |
| 6,331,111 B1 | 12/2001 | Cao | |
| 6,439,888 B1 | 8/2002 | Boutoussov et al. | |
| 6,541,800 B2 | 4/2003 | Barnett et al. | |
| 6,547,423 B2 * | 4/2003 | Marshall et al. | 362/333 |
| 6,560,038 B1 | 5/2003 | Parkyn, Jr. et al. | |
| 6,639,360 B2 * | 10/2003 | Roberts et al. | 313/512 |
| 6,692,251 B1 | 2/2004 | Logan et al. | |
| 6,719,559 B2 * | 4/2004 | Cao | 433/29 |
| 6,832,849 B2 * | 12/2004 | Yoneda et al. | 362/551 |
| 6,857,873 B2 | 2/2005 | Bianchetti et al. | |
| 6,871,983 B2 | 3/2005 | Jacob et al. | |
| 6,896,381 B2 * | 5/2005 | Benitez et al. | 359/858 |
| 7,029,277 B2 * | 4/2006 | Gofman et al. | 433/29 |
| 7,066,733 B2 * | 6/2006 | Logan et al. | 433/29 |
| 7,163,318 B2 * | 1/2007 | Panagotacos et al. | 362/294 |
| 2002/0115037 A1 | 8/2002 | Cao | |
| 2003/0076034 A1 * | 4/2003 | Marshall et al. | 313/512 |
| 2004/0126730 A1 | 7/2004 | Panagotacos et al. | |

FOREIGN PATENT DOCUMENTS

WO     WO 00/67048 A2     11/2000

OTHER PUBLICATIONS

*The Optics of Nonimaging Concentrators: Light and Solar Energy*, Welford, et al., Academic Press, 1978.

*Nonimaging Optics*, Winston, et al., Academic Press, 2004.

* cited by examiner

SECTION A-A

SECTION A-A

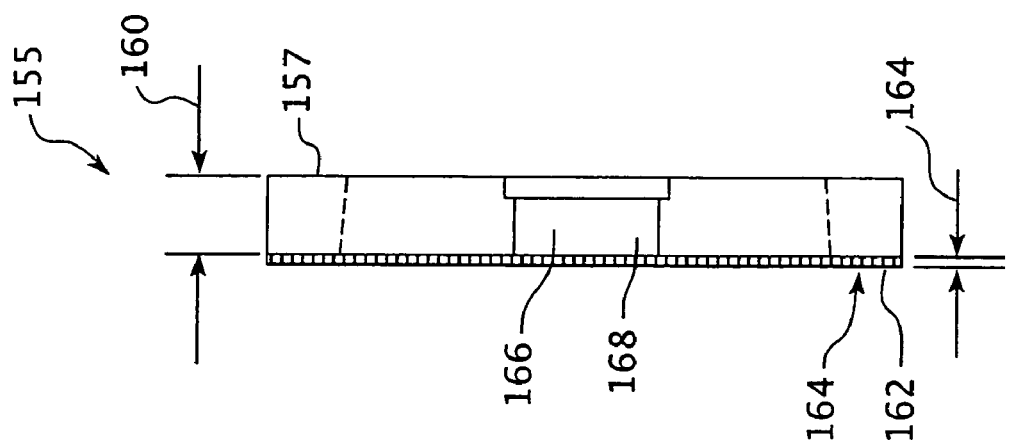
FIG. 21
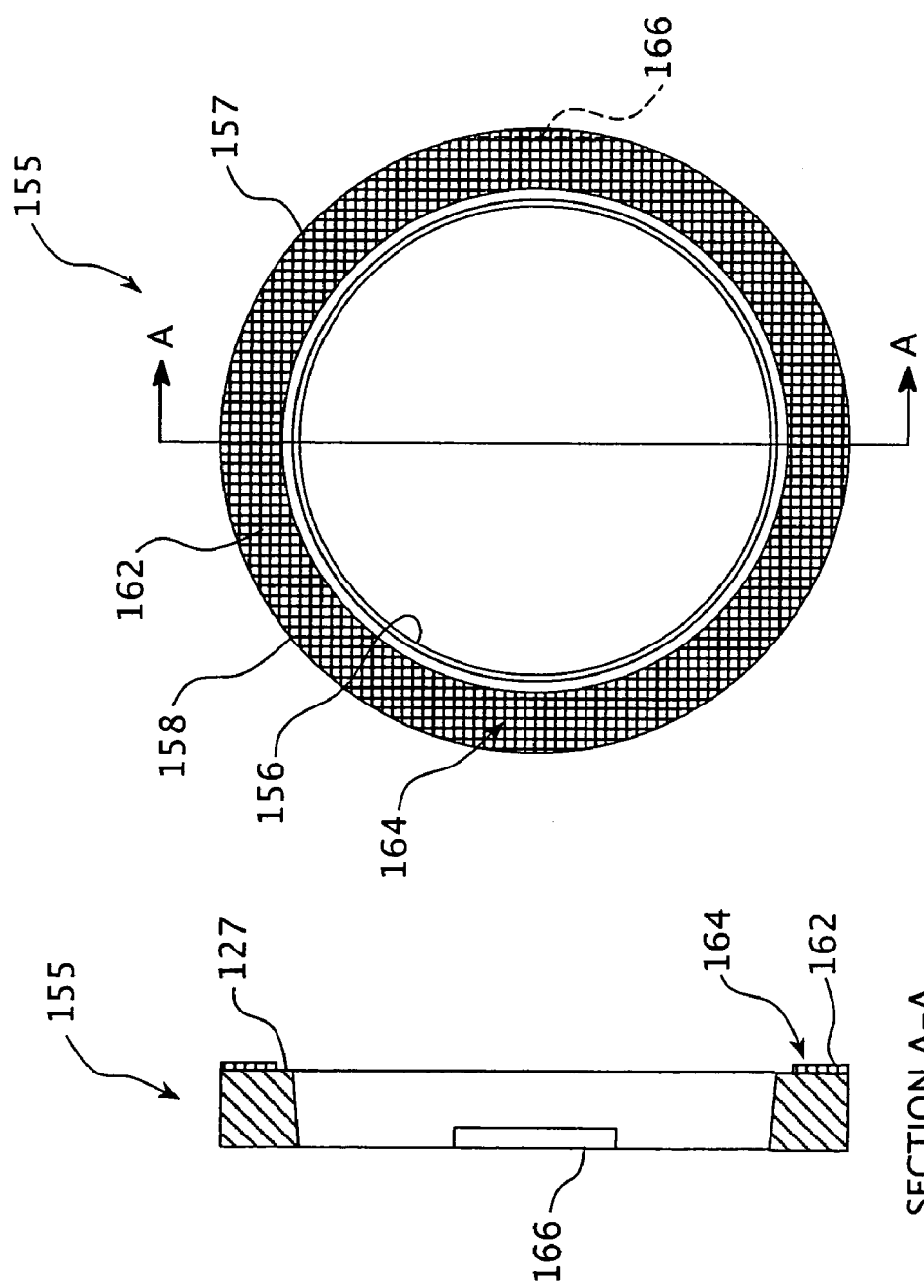
FIG. 19
SECTION A-A
FIG. 20

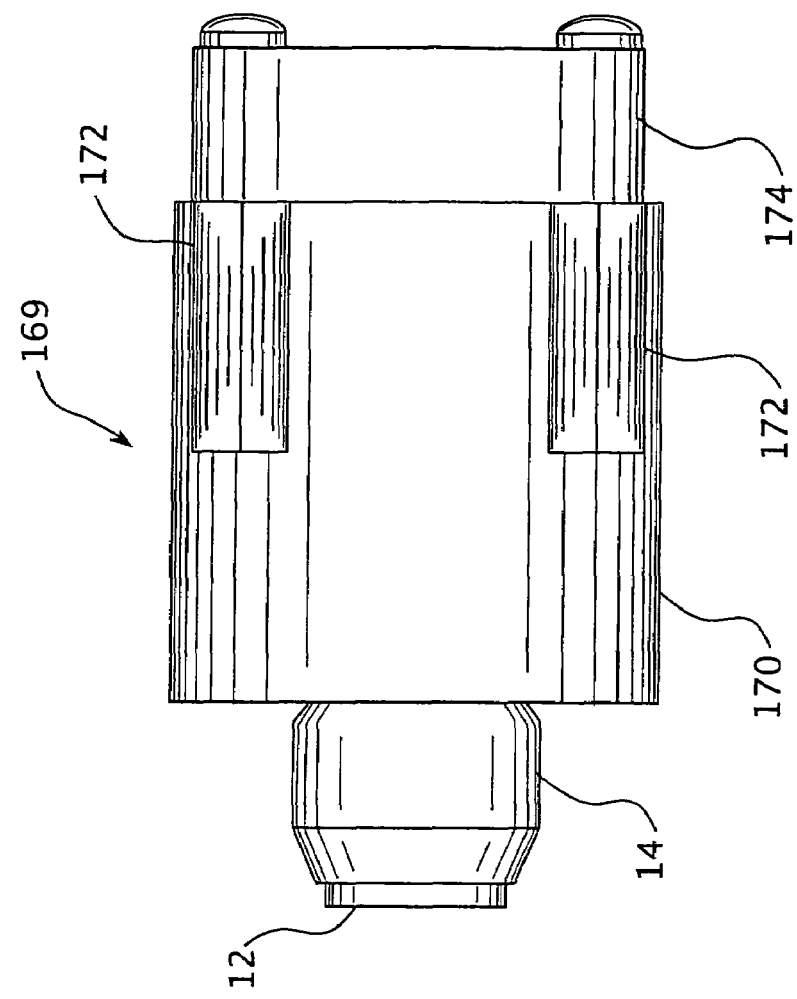
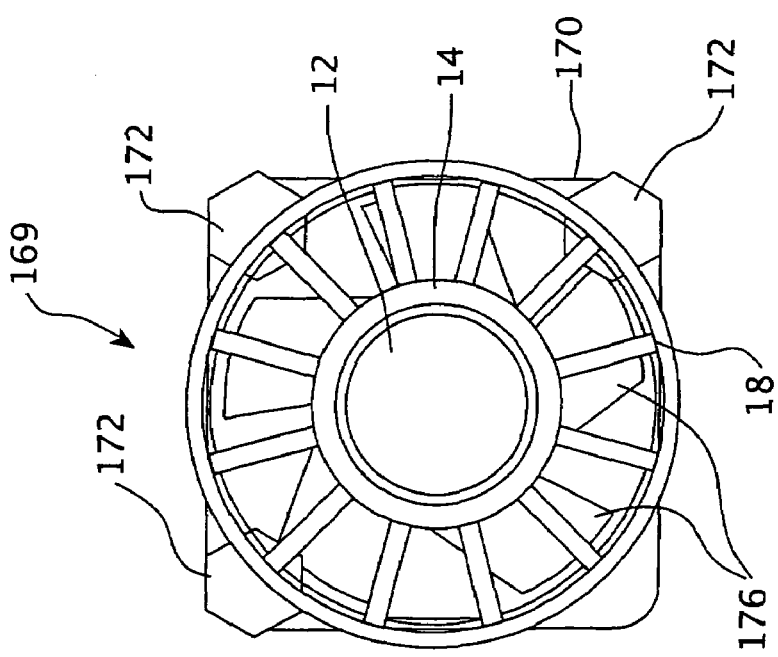
FIG. 22
FIG. 23

ILLUMINATOR ASSEMBLY

CROSS REFERENCE TO RELATED APPLICATIONS

This application claims the benefit under 35 U.S.C. § 119(e) of U.S. Provisional Application No. 60/414,443, filed Sep. 30, 2002, and is a continuation of prior U.S. application Ser. No. 10/675,504, filed Sep. 30, 2003, which issued as U.S. Pat. No. 7,163,318, both of which are incorporated herein by reference in their entirety.

BACKGROUND

The present invention relates generally and in various embodiments to illuminator assemblies. More specifically, the present invention relates generally and in various embodiments to illuminator assemblies including heat sinks.

Although various implementations of the present invention, among many, may be described herein with reference to the specific illustrative embodiments related to particular applications, those skilled in the art will understand that the invention is not in any way intended to be, nor should be, limited to such embodiments and/or applications. Those having ordinary skill in the art and reference to the description of the embodiments disclosed and described herein will recognize that additional modifications, applications, and other embodiments may fall within the scope of the claimed invention, and that there may be additional fields in which the present invention may be practiced.

Compact sources of light are needed for a variety of applications in dentistry and surgery such as surgical cutting, curing of dental composite materials, and activating tooth-whitening materials, for example. Furthermore, dentists may use high intensity light for correcting diseases or defects in hard tissues such as the enamel and dentin portions of the teeth where drills are normally used. In other applications, for example, dentists may use high intensity light for curing a variety of resins and composites in a patient's mouth and for bleaching teeth. Dental composite curing and teeth bleaching application generally require sources of light that emit light having wavelengths in the ultra violet (UV) portion of the spectrum. Surgeons may use high power/high intensity sources of light in certain applications for correcting diseases or defects in soft tissues for which scalpels and other similar surgical cutting instruments are normally used. Cutting applications also may require sources of light that emit light having wavelengths in various portions of the spectrum.

Working in small confined areas such as a patient's mouth, for example, requires that the source of light be compact in size and highly maneuverable. Recent advances in solid state semiconductor technology in the field of laser diodes and light emitting diodes (LEDs) have enabled the miniaturization of these sources of light. Although compact in size, these solid state sources of light generally do not generate an adequate amount of power for the applications described above. When conventional solid state sources of light are driven with higher electrical input power to generate higher optical output power, thermal management becomes difficult and is an important obstacle to overcome in order to provide a source of light having enough intensity in optical output power to make it useful for certain dental and surgical applications, and other fields that may require a high intensity source of light for working in confined areas.

SUMMARY

In one general respect, embodiments of the present invention are directed to an apparatus that includes a lens having a light entrance end forming a recess, a heat sink having an end portion facing the recess, a light source positioned to transmit light via the recess into the lens in thermal communication with the heat sink, wherein heat generated by the light source is conducted to the heat sink.

In another general respect, embodiments of the present invention are directed to a method of providing optical radiation that includes providing a light source that emits light; using a heat sink member to stabilize the temperature of the diode light source, the heat sink member having an end portion facing a recess; transmitting light from the light source via the recess into a lens; transmitting heat generated by the light source into the heat sink; and delivering optical radiation through the lens having a light entrance end forming the recess.

In yet another general respect, embodiments of the present invention are directed to a method of treating a tooth that includes applying a tooth whitening material to a tooth; allowing the tooth to be exposed to the material in the absence of activating light for a substantial period of time; utilizing an array of diodes to produce activating light having a wavelength in the range 400-600 nm; emitting the light forwardly toward a concave wall defined by a lens; and applying the activating light to the material at a power level of 100-600 mW for a period of 20-40 seconds.

In still another general respect, embodiments of the present invention are directed to a method of curing a dental composite material, that includes applying a dental composite material to a tooth; utilizing an array of diodes to produce activating light having a wavelength in the range 400-600 nm; emitting the light forwardly toward a concave wall defined by a lens; and applying the activating light to the dental material at a power level of 100-200 mW for a period of 2-5 seconds.

Other apparatuses, systems, and/or methods according to embodiments of the present invention will be or become apparent to one with skill in the art upon examination of the following drawings and detailed description. It is intended that all such additional apparatuses, systems, and/or methods be included within this description, be within the scope of the present invention, and be protected by the accompanying claims.

DESCRIPTION OF THE DRAWINGS

Embodiments of the present invention are described herein in conjunction with the following figures, wherein:

FIGS. 19, 20, and 21 show an end view, a sectioned view, and a side view, respectively, of another embodiment of a terminal board; and FIGS. 22 and 23 show a side view and an end view, respectively, of one embodiment of an illuminator assembly.

DESCRIPTION

It is to be understood that the figures and descriptions of the various embodiments of present invention described herein, among others, have been simplified to illustrate representative elements of various embodiments of illuminator assemblies comprising various embodiments of light source assemblies that may be used in a variety of applications, such as, for example, applications requiring the use of high intensity light when working in confined quarters. The representative elements described herein are relevant for a clear understanding of the present invention. For purposes of clarity, however, other specific elements that would not facilitate a better or clearer understanding of the present invention may not be described herein. Those of ordinary skill in the art will appreciate, however, that these and other elements may be found in conventional illuminator assemblies and may be readily understood.

Figure 1:
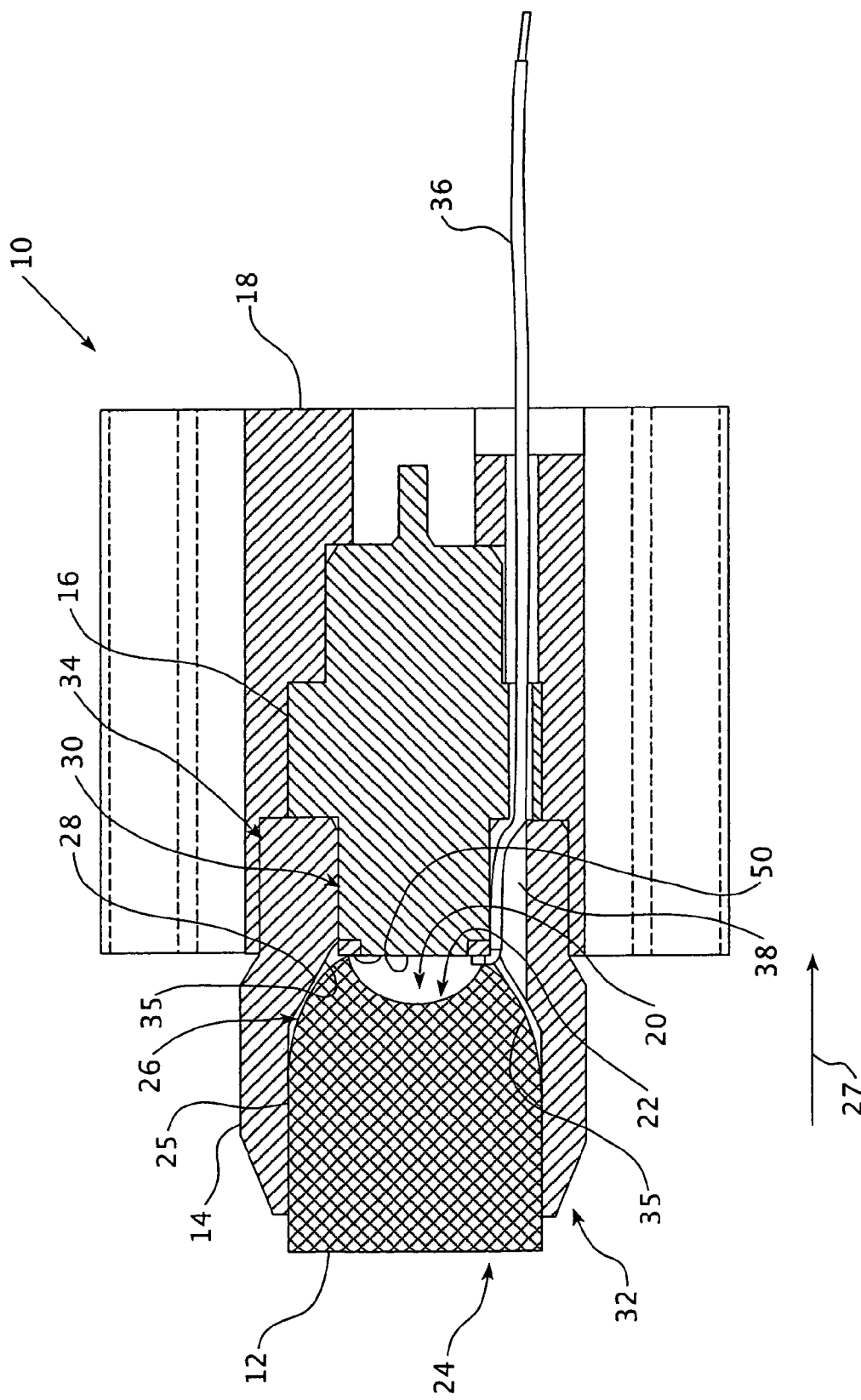
FIG. 1 is a sectioned assembly view of one embodiment of an illuminator assembly.

FIG. 1 is a sectioned assembly view of one embodiment of an illuminator assembly 10 in accordance with the present invention. The illuminator assembly 10 may comprise a variety of components such as a lens 12, a lens holder 14, a first heat sink 16, and, optionally, a second heat sink 18, for example. The heat sink 16, 18 may be any substance or device for the absorption or dissipation of heat generated from a process, electronic device, or light source, for example. In one embodiment of the present invention, the lens 12 and the first heat sink 16 may be coaxially aligned. In one embodiment of the present invention, the first heat sink 16 and the lens holder 14 also may be coaxially aligned. In one embodiment of the present invention, the illuminator assembly 10 may include a housing 170 (e.g., see FIGS. 22, 23) extending about the first heat sink 16 and is in coaxial relation therewith. Further, the lens holder 14 may include an end portion that is received into the housing 170. Also, in one embodiment of the present invention, the first heat sink 16 may act as a primary heat sink for conducting heat away from the light source while the second heat sink 18 may act as a secondary heat sink for conducting heat away from the first heat sink 16.

With reference to the embodiments depicted in FIGS. 1-23, the lens 12 may include, for example, a light entrance end 20 forming a recess 22 and a light exit end 24 where light generated by a light source assembly 50 (e.g., see FIGS. 9, 10, 17) located on an end portion 30 of the first heat sink 16 is emitted. The lens 12 also may include a forward cylindrical portion 25 and a rearward portion 26 extending about the recess 22 that defines an outer surface 28 that tapers in a direction 27 toward the first heat sink 16 and/or the second heat sink 18.

The lens holder 14 may include a front portion 32 that extends about the recess 22 of the lens 12 and may include a rear portion 34 for receiving the end portion 30 of the first heat sink 16. Thus the end portion 30 of the first heat sink 16 projects endwise into the lens holder 14. The lens holder 14 also may define an inner wall 35 that tapers in a direction 27 toward the first heat sink 16 and/or the second heat sink 18. The lens's tapering outer surface 28 also may extend into the tapered portion of the lens holder's inner wall 35. The lens's outer surface 28 also tapers in the direction 27 toward the first heat sink 16 and/or the second heat sink 18 and is oriented in adjacent relation to the lens holder's 14 inner wall 35.

The illuminator assembly 10 in accordance with one embodiment of the present invention also may include a first current carrying wire 36 that extends between the lens holder 14 and the first heat sink 16 and/or the second heat sink 18. The first current carrying wire 36 may be used to supply electrical current to the light source. The first current carrying wire 36 may be received in an opening 38 formed in the lens holder 14.

Figure 2:
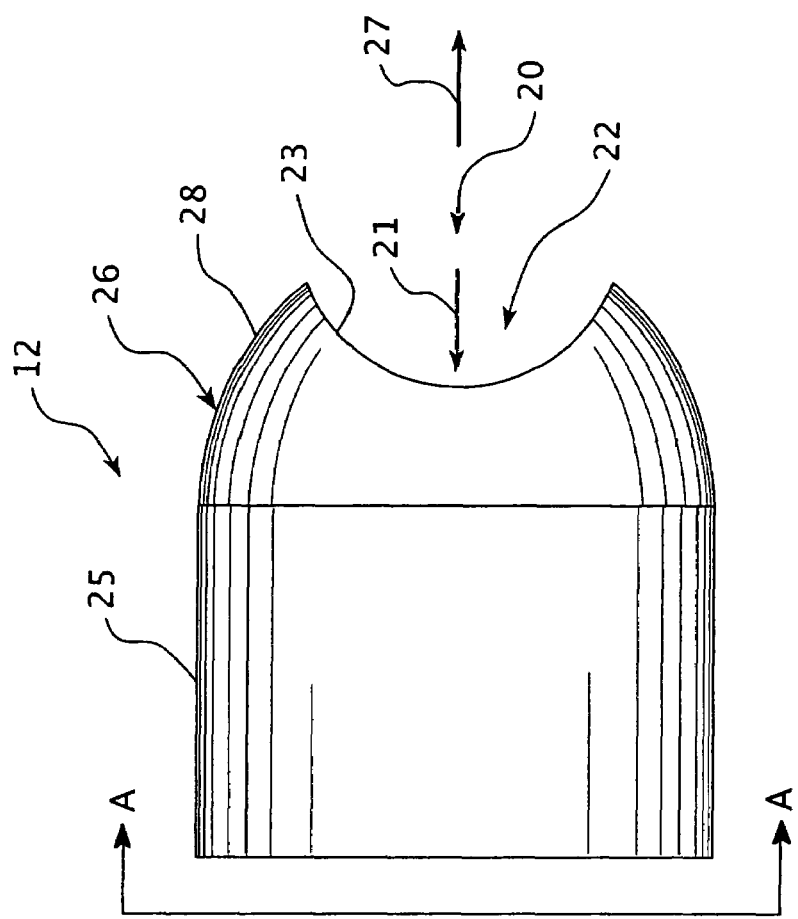
FIGS. 2 and 3 are side and end views, respectively, of one embodiment of a lens.
Figure 3:
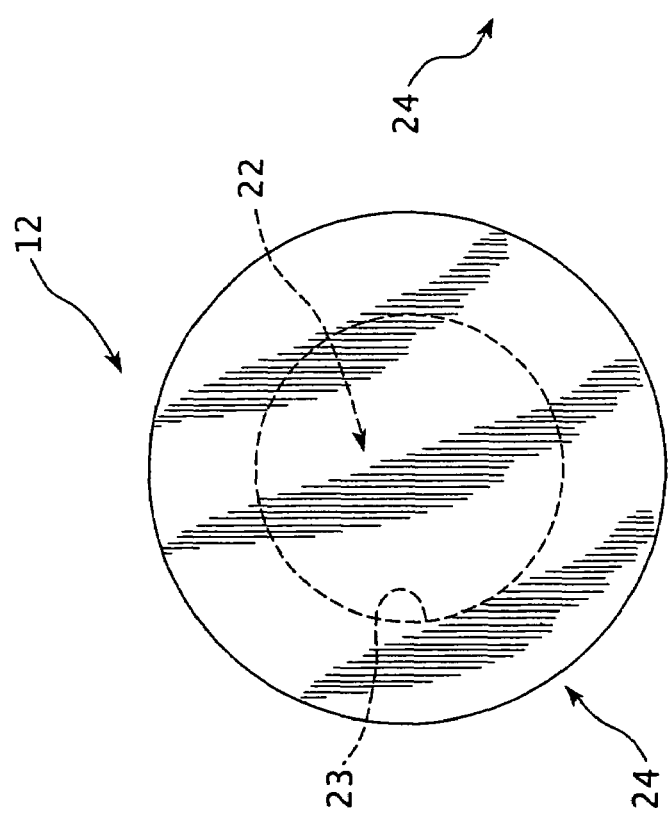

FIGS. 2 and 3 show a side view and an end view A-A, respectively, of one embodiment of the lens 12 component of the illuminator assembly 10 according to the present invention. As discussed previously, the lens 12 may include, for example, the light entrance end 20 forming the recess 22 and the light exit end 24 for emitting the light generated by the light source assembly 50. As illustrated, the lens 12 has a forward cylindrical portion 25 and a rearward arcuate portion 26 that extends about the recess 22. The arcuate portion 26 defines an outer surface 28 that tapers in the direction 27 toward the first heat sink 16 and/or the second heat sink 18. In one embodiment of the present invention, the recess 22 may be re-entrant into the lens 12. The lens 12 may include a rearward wall 23 that is concave in a direction 21 toward the recess 22. In one embodiment of the present invention, the recess 22 may be filled with a light transmitting material, such as, for example, a light transmitting plastic material. For example, the recess 22 may contain an optical plastic material having a predetermined index of refraction. In one embodiment, the index of refraction of the optical plastic material may be substantially the same as the index of refraction as the lens 12 material. Further, the optical plastic material contained in the recess 22 may be curable by light having a wavelength in the ultra-violet (UV) portion of the optical spectrum, for example. The lens 12, for example, may be a non-imaging lens and may be formed of a variety of materials such as optical polycarbonate, for example. In one embodiment of the present invention, the lens 12 may be a total internal reflection (TIR) lens.

Figure 6:
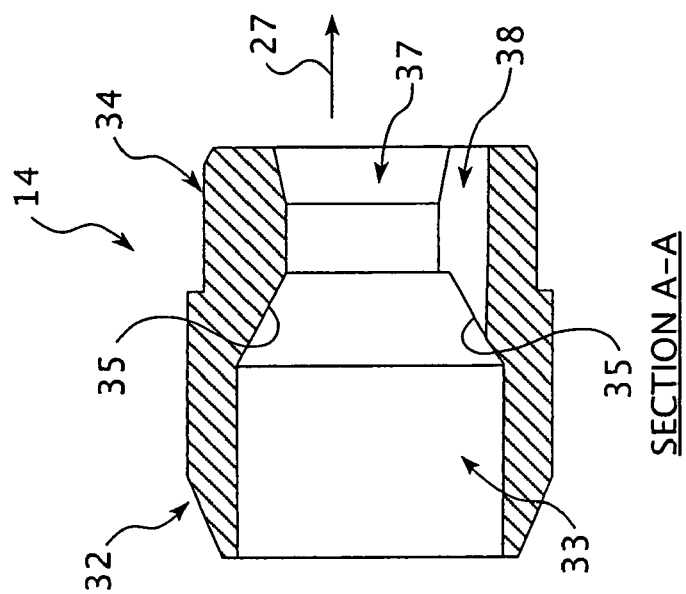
FIGS. 4, 5, and 6 are side, end, and sectioned views, respectively, of one embodiment of a lens holder.
Figure 5:
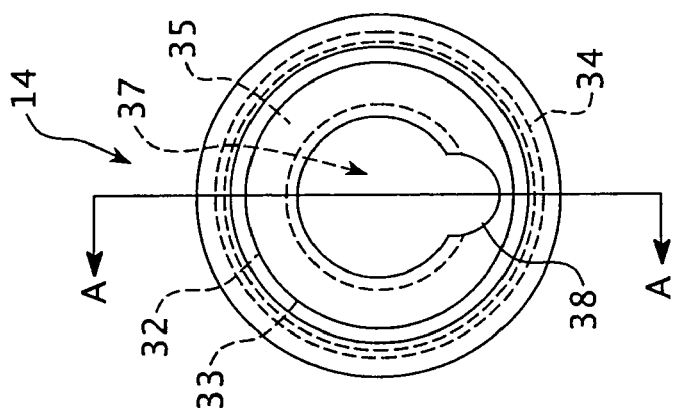
Figure 4:
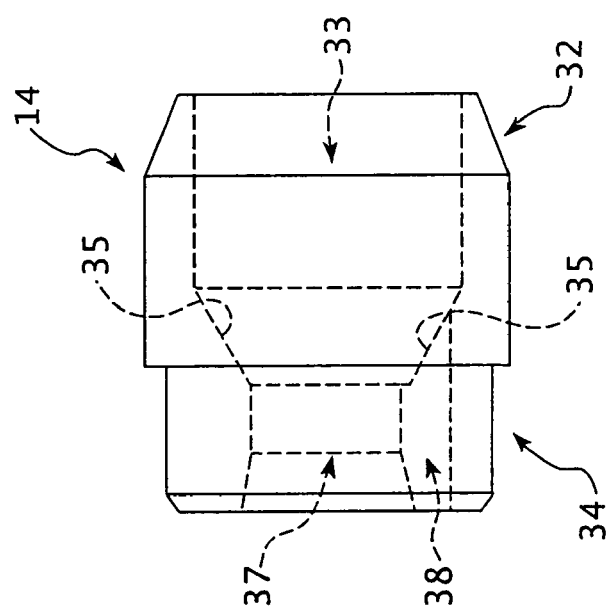

FIGS. 4, 5, and 6 are side, end, and sectioned views, respectively, of one embodiment of the lens holder 14 component of the illuminator assembly 10 according to the present invention. The front portion 32 of the lens holder 14 defines a first cavity 33 for receiving the light entrance end 20 of the lens 12. The front portion 32 and the inner wall 35 of the lens holder 14 extend about the recess 22 of the lens 12. The rear portion 34 of the lens holder 14 defines a second cavity 37 for receiving the end portion 30 of the first heat sink 16 such that the end portion 30 of the first heat sink 16 including the light source assembly 50 projects endwise into the lens holder 14. The inner wall 35 of the lens holder 14 tapers to a smaller diameter in the direction 27 toward the first heat sink 16 and/or the second heat sink 18. The tapering outer surface 28 of the lens 12 extends into the tapered inner wall 25 portion of the lens holder 14. The outer surface 28 of the lens 12 is in adjacent relation to the inner wall 35 of the lens holder 14 and is tapered toward the first heat sink 16 and/or the second heat sink 18. The lens holder 14 also defines an opening 38 for receiving the first current carrying wire 36 therethrough. In one embodiment of the present invention, the lens holder 14 may be formed of Teflon, for example.

Figure 7:
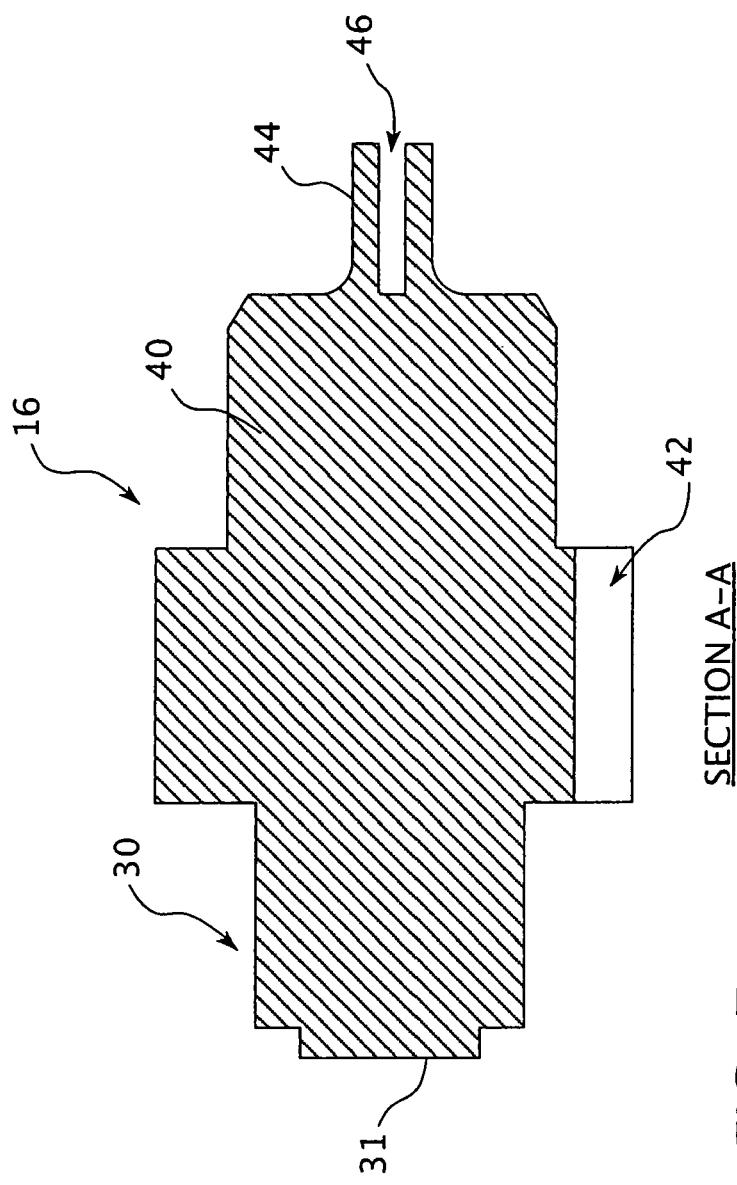
FIGS. 7 and 8 are sectioned and end views, respectively, of one embodiment of a heat sink.
Figure 8:
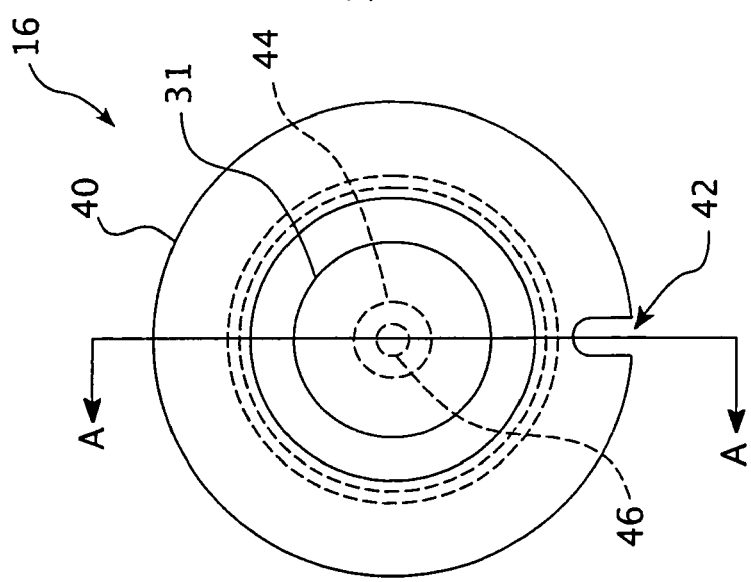

FIGS. 7 and 8 are side and end views, respectively, of one embodiment of the first heat sink 16 component, according to the present invention, where FIG. 7 is a sectioned view. The first heat sink 16 comprises a body portion 40, which may include an end portion 30 that faces the recess 22 portion of the lens 12. The end portion 30 is received into the second cavity 37 defined by the rear portion 34 of the lens holder 14. The end portion 30 also includes a face portion 31 for receiving the light source assembly 50 (e.g., see FIGS. 9 and 10). In one embodiment of the present invention, the face portion 31 of the first heat sink 16 may be gold plated and/or gold/nickel plated such that the face portion 31 is rendered suitable for attaching a semiconductor die or chip directly thereon and is rendered suitable for accepting wire bonds thereon. For thermal management purposes, the light source assembly 50 is placed in thermal communication or in contact with the body portion 40 or end portion 30 of the first heat sink 16 and/or with the second heat sink 18. Thus, the first heat sink 16 acts a thermal conductor and its body portion 40 conducts heat away from the light source assembly 50. The body portion 40 of the first heat sink 16 also may transmit heat generated by the light source assembly 50 to the second heat sink 18 formed about the first heat sink 16. The body portion 40 of the first heat sink 16 also may include a channel 42 formed therein for receiving the first current carrying wire 36 so that electrical current may be supplied to the light source assembly 50 located on the face portion 31 of the first heat sink 16. The body portion 40 of the first heat sink 16 also may include an elongated portion 44, which may define a hollow portion 46 for receiving a second wire 48 (e.g., see FIG. 9) therein.

The body portion 40 of the first heat sink 16 may be formed of a variety of materials that are thermally conductive and/or electrically conductive materials such as, for example, aluminum, brass, bronze, copper, gold, nickel, platinum, steel, and the like, and/or any combinations of such materials including plated forms of such materials. In one embodiment, the first heat sink 16 may be nickel or gold plated copper. In one embodiment of the present invention, the first heat sink 16 may be nickel or gold plated on portions of the body 40 to make electrical connections. In other embodiments, the first heat sink 16 and the second heat sink 18 may be integrally formed.

Figure 10:
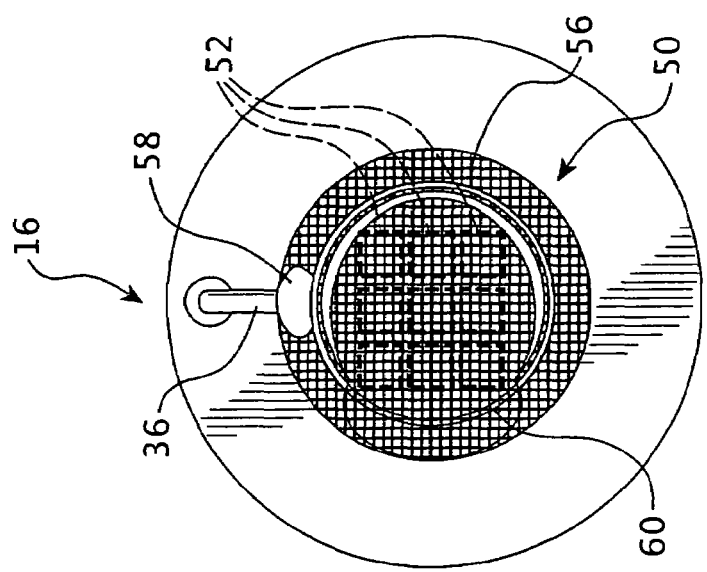
FIGS. 9 and 10 are side and end views, respectively, of one embodiment of a heat sink, FIG. 9 showing wiring to LEDs, which are also shown in FIG. 10.
Figure 9:
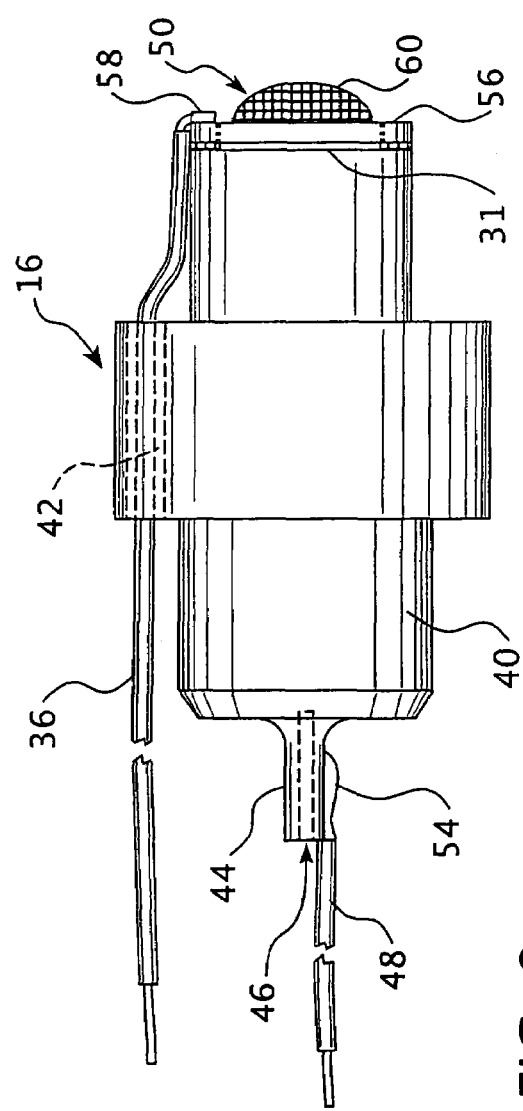

FIGS. 9 and 10 are also side and end views, respectively, of one embodiment of the first heat sink 16 component according to the present invention. The first heat sink 16 is shown wired to one embodiment of a light source assembly 50 according to the present invention. The light source assembly 50, may comprise, for example, a light source 52 including a plurality or array of light emitting diodes 93 (LEDs) in semiconductor die form, and may be arranged in a predetermined manner as shown. The light source assembly 50 is located on the face portion 31 of the first heat sink 16. The light source assembly 50 is positioned such that it faces the recess 22 formed on the light entrance portion 20 of the lens 12. Accordingly, the light emitted from the light source 52 is transmitted via the recess 22 and the material contained in the recess 22. In one embodiment of the present invention, the light source assembly 50 may comprise one or more LED semiconductor die(s) 93 die bonded to the face portion 31 of the end portion 30 of the first heat sink 16. The light source assembly 50 also may include an interface board 56 for making an appropriate physical electrical connection between a light source power supply and the light source 52. At one end, the first wire 36 is electrically connected to the interface board 56 at solder connection 58. At another end, the first wire 36 is connected to a light source power supply. For example, the first wire 36 may supply electrical current to the light source 52 or may provide a return path (e.g., ground) for the light source 52. The interface board 56 also may serve for receiving wire bonds, e.g., from the LED semiconductor dies 93.

A second wire 48 may be electrically attached to the elongated portion 44 of the first heat sink 16 by any well known means of attachment, such as a solder connection 54, a weld, screw, and the like. The second wire 48 also may be attached directly to an outer wall of the body portion as shown in FIG. 9. In one embodiment of the present invention, the body portion 40 of the first heat sink 16 may be connected to an electrical connection of the light source assembly 50 through the second wire 48. The electrical connection may be used to supply power or a return path (e.g., ground) through the second wire 48. Those skilled in the art will appreciate, however, that the second wire 48 may be used as return signal or ground wire, without departing from the scope of the present invention.

The light source 52 may be coated with an optically transmissive encapsulating material 60, such as UV curable adhesive optical acrylic material, for example. In one embodiment of the present invention, the encapsulating material 60 is placed in a mold such that its shape conforms to the surface contour of the recess 22 formed in the light entrance end 20 of the lens 12. Conforming the shape of the encapsulating material 60 to the contour of the recess 22 helps to transmit the light generated by the light source 52 to the lens 12 and through the light exit end 24 of the lens 12. The light source assembly 50 will be discussed below in more detail with respect to FIGS. 15-21.

Figure 12:
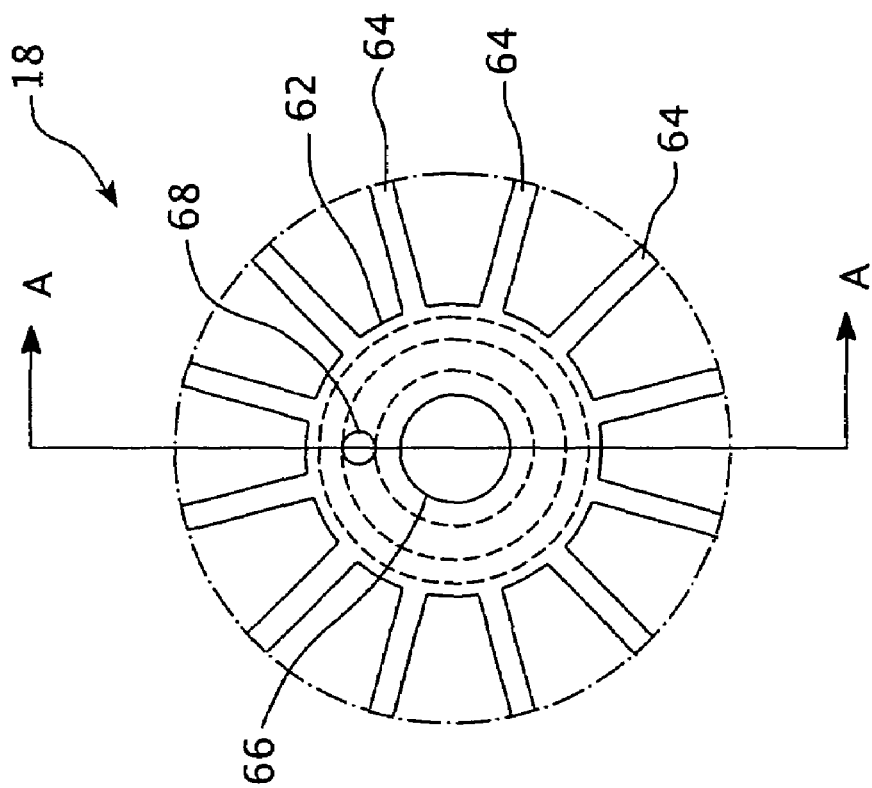
FIGS. 11 and 12 are sectioned and end views, respectively, of one embodiment of a secondary heat sink.
Figure 11:
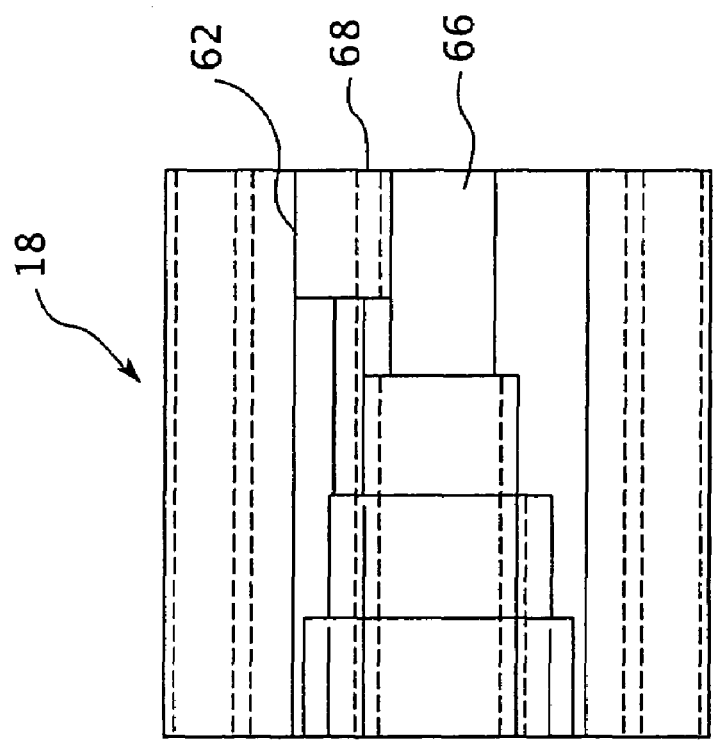
Figure 14:
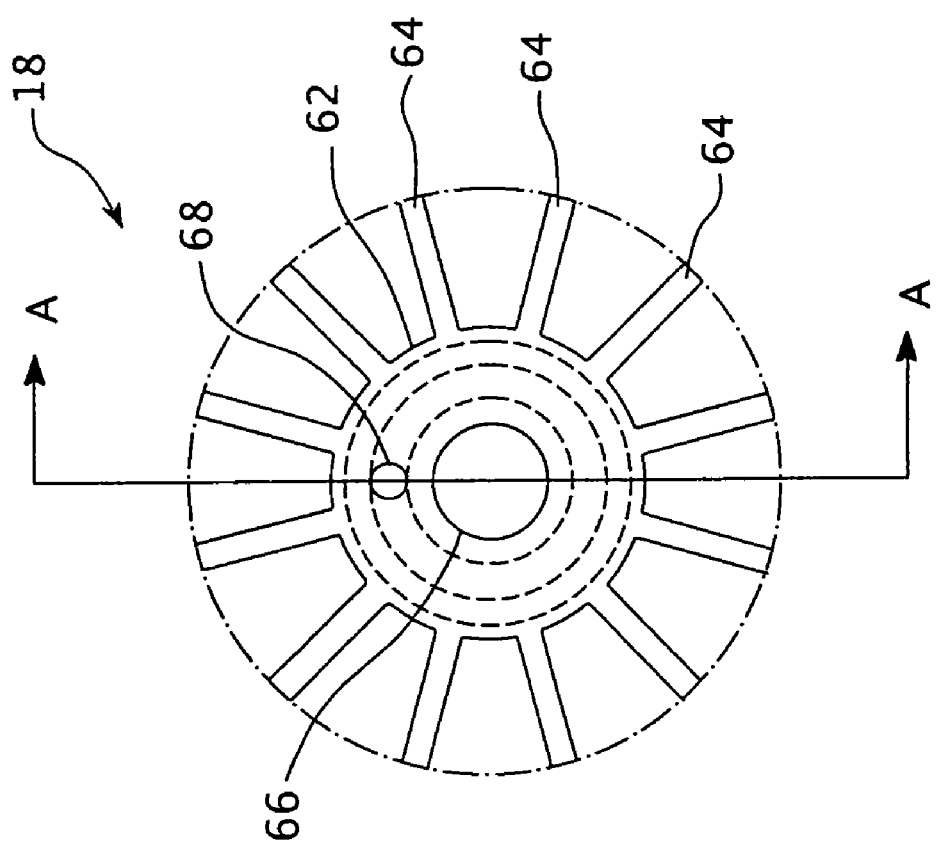
FIG. 14 is an end view of one embodiment of the heat sink shown in FIGS. 11, 12, and 13.
Figure 13:
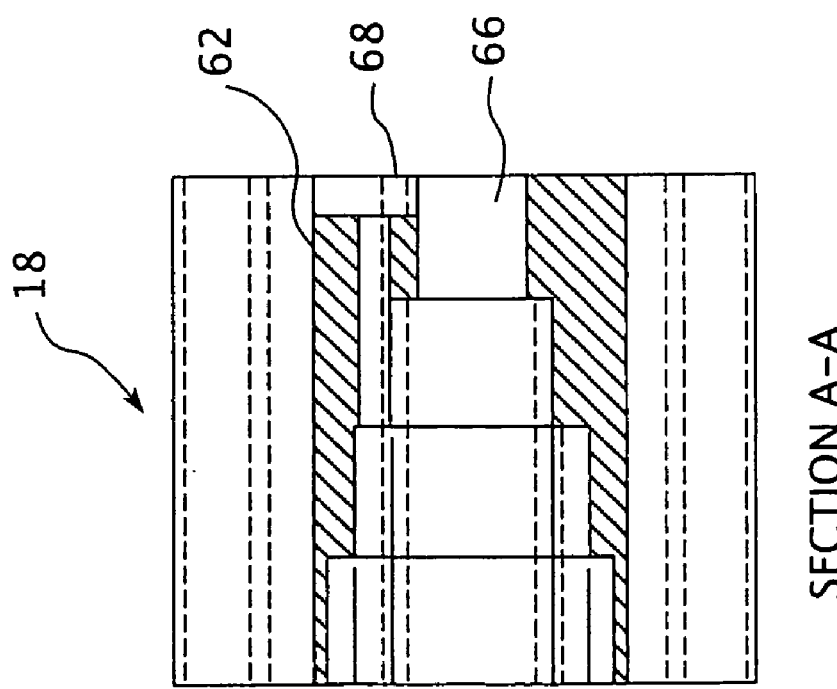
FIG. 13 is a sectioned view of one embodiment of the heat sink shown in FIGS. 11 and 12.

FIGS. 11 and 12 are sectioned and end views, respectively, of one embodiment the second heat sink 18 component of the illuminator assembly 10 according to the present invention. FIG. 13 is a sectioned view of the second heat sink 18 component and FIG. 14 is an end view thereof. The second heat sink 18 includes a body 62 having a plurality of fins 64 for conducting heat away from the first heat sink 16. The secondary heat sink body 62 defines an opening 66 for receiving the second wire 48 therethrough. The secondary heat sink body 62 also may define a passage or channel 68 for receiving the first wire 36 therethrough. The body 62 may be formed of a plurality of thermally conductive materials such as, for example, aluminum, brass, bronze, copper, gold, nickel, platinum, steel, and the like, and/or any combinations of such materials including plated forms of such materials. The materials may be the same or different form the first heat sink 16.

Figure 16:
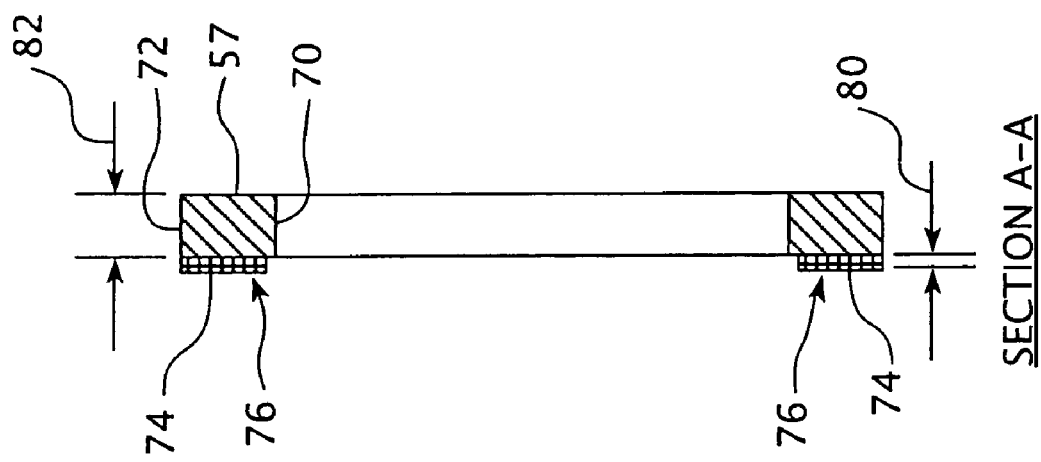
FIGS. 15 and 16 show one embodiment of a terminal board.
Figure 15:
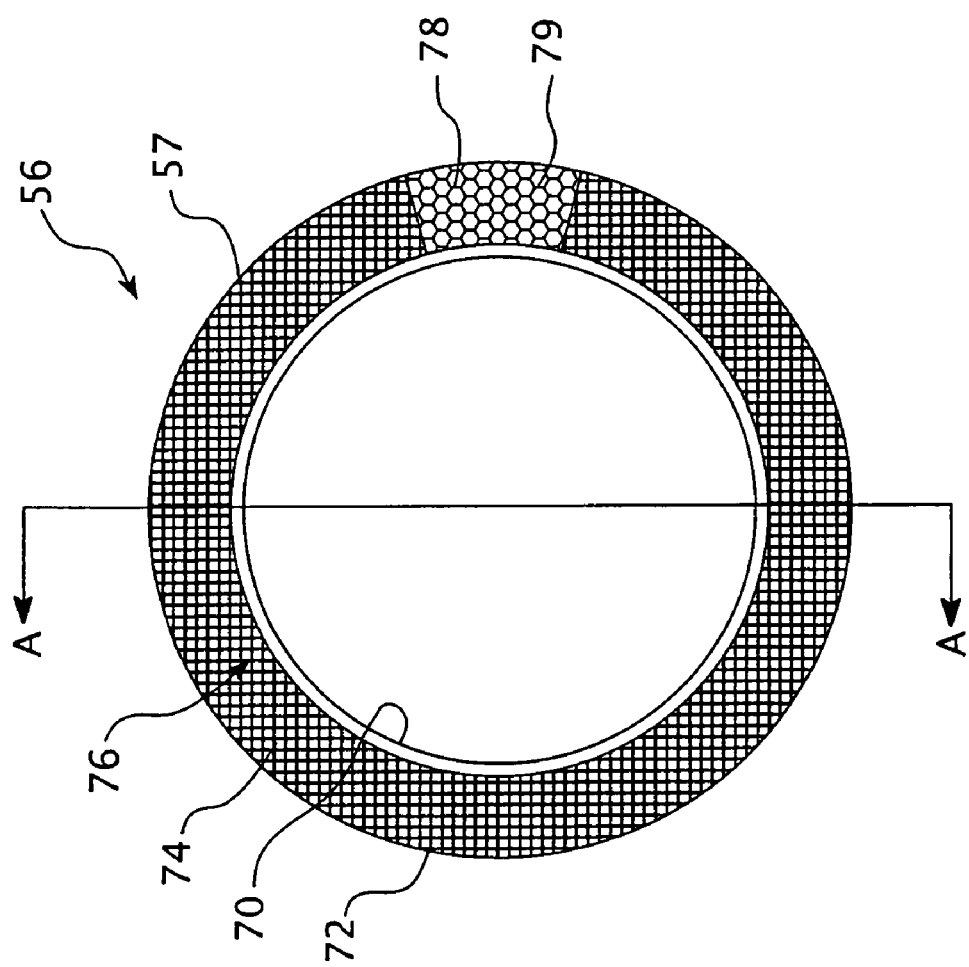

FIGS. 15 and 16 show a top view and sectioned view, respectively, of one embodiment of the interface board 56 according to the present invention. The interface board 56 may comprise, for example, a substrate 57, which may be in the form of a ring defining an aperture or may have a shape that conforms to the face portion 31 of the first heat sink 16. The substrate 57 may include, for example, an inner wall 70 and an outer wall 72. The substrate 57 may have a thickness 82 of about 0.025 inches, for example.

In one embodiment of the present invention, the substrate 57 may be formed of ceramic or any other material suitable for depositing metallic films thereon, such as for example, alumina, glass, silicon or other semiconductor, aluminum, copper, gold, silver, nickel, and the like. In one embodiment of the present invention, the substrate 57 may include a first metallic conductive film 74 processed on a top surface 76 thereof. In one embodiment of the present invention the film 74 may be a thin film of gold, or other metal, suitable for wire bonding thereto, for example. The film thickness 80 may range, for example, from about 5 to about 10 microns. In one embodiment of the present invention, the top surface 76 of the substrate 57 may include a conductive pad 78 having a second metallic conductive film 79 processed thereon suitable for making a solder, or other electrical connection, thereto. Thus the conductive pad 78 may form an electrical connection between the first wire 36 and the interface board 56. The second metallic conductive film 79 may be, for example, a platinum silver paste having a thickness ranging from about 10 to about 16 microns, for example. The second metallic conductive film 78 may be suitable, for example, for attaching the first wire 36 to the interface board 56 at a solder connection 58 for supplying electric current to the light source 52, for example. The first and second metallic conductive films 74, 79 may be processed onto the surface 76 of the interface board 56 by any one of a plurality of well known methods for processing such films, such as, for example, sputtering, vacuum deposition, screen printing and firing, and the like.

Figure 17:
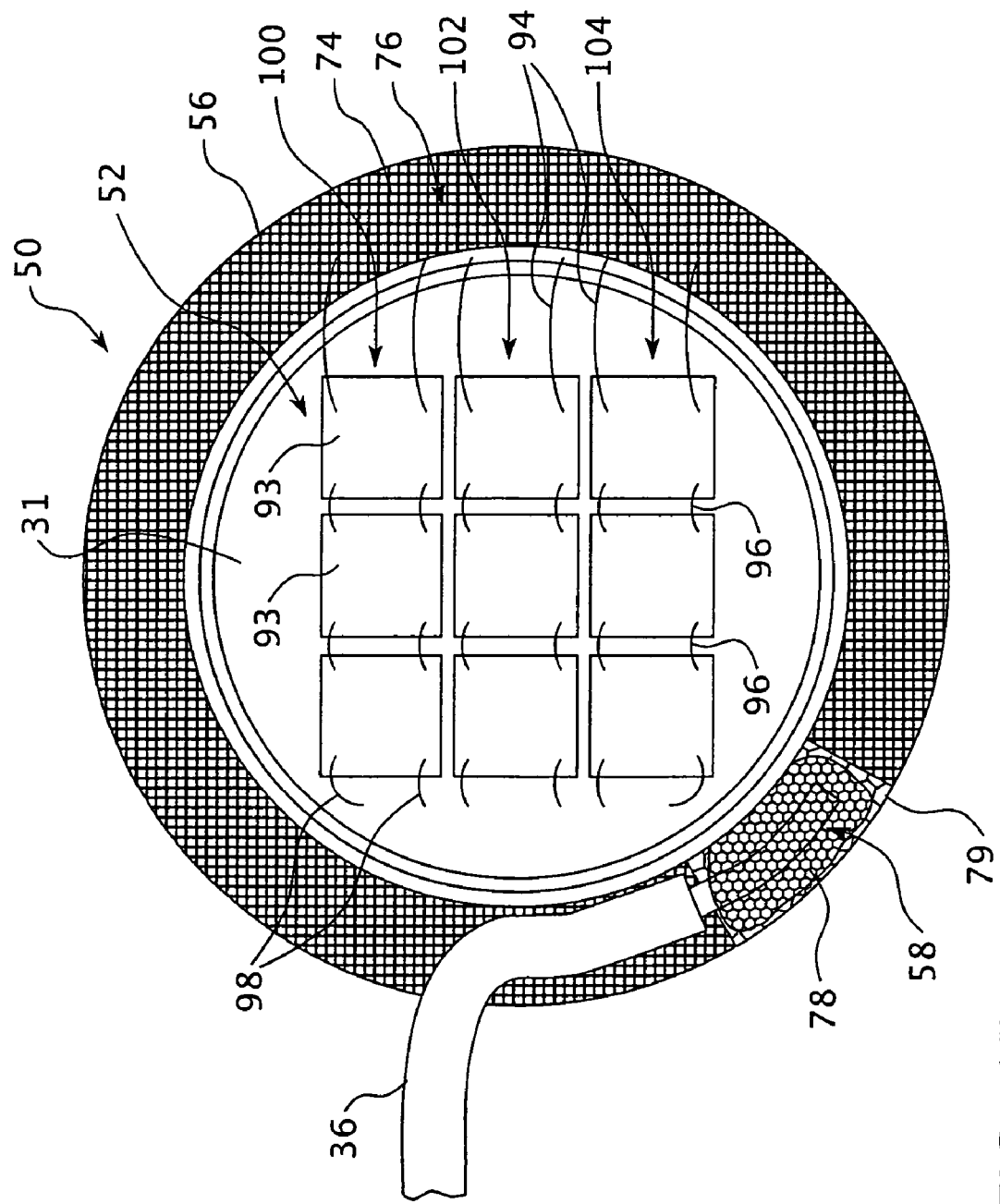
FIG. 17 is an end view of one embodiment of a light source assembly showing an LED array wiring configuration.

FIG. 17 is an end view of one embodiment of the light source assembly 50, shown in greater detail, including a nine up wiring configuration of the LED array 52. The LED array 52 comprises a plurality of LEDs semiconductor dies 93 die bonded to the face portion 31 of the first heat sink 16, for example. As discussed previously, the face portion 31 may provide a return path or ground connection to the power supply for the light source assembly 50. The interface board 56 also comprises the metallic conducting film 74 deposited on the surface 76 thereof. The metallic conducting film 76 may be chosen for wire bonding any suitable type of wire bonds, such as, for example, gold or aluminum wire bonds. The LED semiconductor dies 93 may be wire bonded to the top surface 76 of the interface board 56 via wire bonds 94, for example. Electric current may be supplied to the LED semiconductor dies 93 via the wire bonds 94. The LED semiconductor dies 93 may be interconnected to each other via wire bonds 96. The LED semiconductor dies 93 also may be connected to the face portion 31 of the first heat sink 16 via wire bonds 98, for example. As shown, the LED array 52 is formed of three banks of LEDs 100, 102, 104, each comprising three LED semiconductor dies 93 interconnected in series, for example. As discussed previously, the electrically conductive wire 36 may be connected to the interface board 56 through solder connection 58 and may be used to supply electric current to the light source assembly 50. The solder connection 58 may be formed, for example, over the conductive pad 78 through the metallic conducting film 79 deposited thereon. In one embodiment of the present invention the metallic conducting film 79 may be a palladium silver compound processed over the conductive pad 78, for example.

Figure 18:
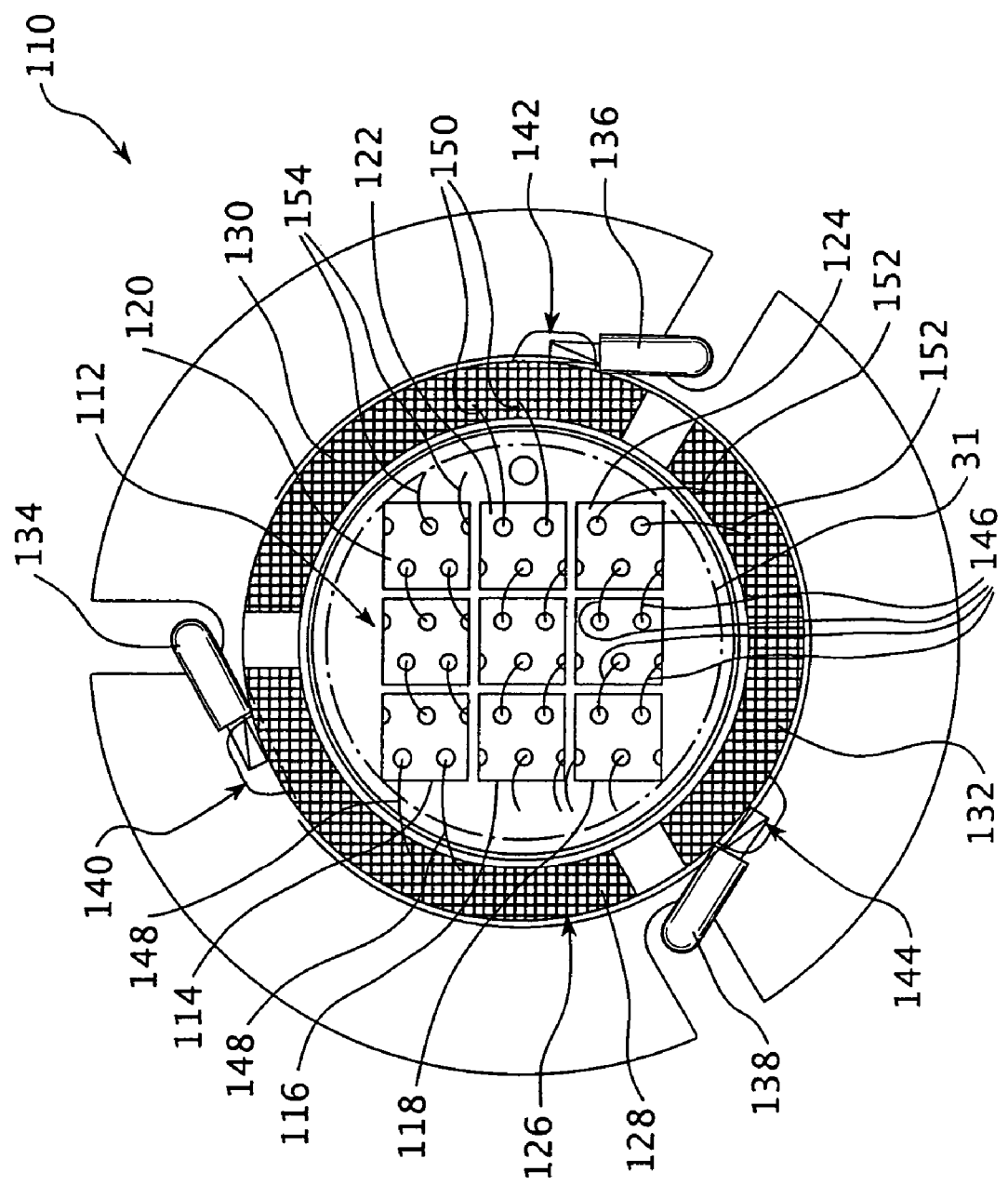
FIG. 18 is an end view of another embodiment of a light source assembly showing an LED array wiring configuration.

FIG. 18 is an end view of another embodiment of a light source assembly 110 comprising a light source 112 formed, for example, of one or more LED semiconductor dies 120, 122, 124. The light source 112 comprises a plurality of LED banks 114, 116, 118 in die form bonded to the face portion 31 of the first heat sink 16, for example. Each LED bank 114, 116, 118 may comprise one or more LED semiconductor dies 120, 122, 124 that emit light of a different wavelength. For example, the first LED bank 114 may comprise an LED semiconductor die 120 that emits red light having an intensity of up to about 700 lumen, for example. The second LED bank 116 may comprise an LED semiconductor die 122 that emits blue light having an intensity of up to about 100 lumen, for example. The third LED bank 118 may comprise an LED semiconductor die 124 that emits green light having an intensity of up to about 100 lumen. Those skilled in the art will appreciate, however, that embodiments of the present invention is not limited to these wavelengths and may include any combination of LED semiconductor dies 120, 122, 124 that emit light of any wavelength without departing from the scope of the present invention, including for example, LED semiconductor dies that emit amber light having an intensity of up to about 70 lumen.

As discussed previously the face portion 31 of the first heat sink 16 provides one of the electrical connections to the light source assembly 110. For example, in one embodiment of the present invention, the face portion 31 may provide a ground connection or electric current return path to a light source power supply, for example. The light source assembly 110 also may comprise an interface board 126 including a plurality of individual wire bondable conductive pads 128, 130, 132, wherein each individual conductive pad 128, 130, 132 includes the metallic conducting film 74 deposited on the surface thereof, for example, and the conductive film 74 is suitable for wire bonding the LED semiconductor dies 120, 122, 124 to the interface board 126. In one embodiment of the present invention, the three individual conductive pads 128, 130, 132 are spaced 120° apart. Further, in one embodiment, the LED semiconductor dies 120, 122, 124 may be die bonded to the face portion 31 of the first heat sink.

Electrical current may be separately supplied and separately controlled to each LED bank 114, 116, 118 through electrically conducting wires 134, 136, 138, respectively. Each wire 134, 136, 138 is connected to each conductive pad 128, 130, 132, respectively, via the solder connections 140, 142, 144, respectively. Therefore the relative amount of electrical current supplied to each LED bank 114, 116, 118 may individually controlled so that the relative light output intensity of each LED bank 114, 116, 118 may be controlled. Accordingly, the combined light output of each LED bank 114, 116, 118 may be varied through a wide range of wavelengths at various levels of intensity.

The individual LED semiconductor dies 120, 122, 124 forming any one of the LED banks 114, 116, 118 may be interconnected to each other through interconnecting wire bonds 146. The first LED bank 114 may be connected to the conductive pad 128 via wire bonds 148. Similarly, second and third LED banks 116, 118 may be connected to conductive pads 130, 132 via wire bonds 150, 152, respectively. Each LED bank 114, 116, 118 may be connected to the face portion 31 of the first heat sink through wire bonds 154.

FIGS. 19, 20, and 21 show a top view, sectioned view, and side view, respectively, of another embodiment of an interface board 155 according to the present invention. In one embodiment of the present invention, the interface board 155 comprises a substrate 157 in the form of a ring having an inner wall 156 and an outer wall 158. In one embodiment of the present invention, the substrate 157 may be formed of ceramic or any other material suitable for depositing metallic films thereon, such as for example, alumina, glass, silicon or other semiconductor, aluminum, copper, gold, silver, nickel, and the like. The substrate 157 thickness 160 may be about 0.04 inches, for example.

In one embodiment of the present invention, the interface board's 155 substrate 157 may include a first metallic conductive film 162 processed on a top surface 164 thereof.

In one embodiment of the present invention the film 162 may be a thin film of gold, or any other metal, suitable for wire bonding, for example. The film thickness 164 may be any thickness that provides sufficient electrical conductivity, such as, a range from about 5 to about 10 microns, for example. In one embodiment of the present invention, the top surface 164 of the substrate 157 also may include a conductive pad 166 having a second metallic conductive film 168 processed thereon suitable for forming an electrical connection between any of the wires 36, 134, 136, 138 and the interface board 155 through the various solder connections 58, 140, 142, 144. The second metallic conductive film 168 may be, for example, a palladium silver paste having a thickness ranging from about 10 to about 16 microns, for example. The second metallic conductive film 168 may be suitable, for example, for attaching any of the wires 36, 134, 136, 138 to the interface board 155 to provide electric current to the light source assembly 50, 110. The first and second metallic conductive films 162, 166 may be processed onto the surface 164 of the interface board 155 using any one of a plurality of well known methods for processing such films, such as, for example, sputtering, vacuum deposition, screen printing and firing, and the like.

FIGS. 22 and 23 show a side view and a front view, respectively, of one embodiment of a light source assembly 169 according to the present invention. The light source assembly 169 includes the lens 12, the lens holder 14, the first heat sink 16, the second heat sink 18, a housing 170, one or more standoffs 172, and a fan assembly 174 including fan blades 176. The housing 170 extends about the first heat sink 16 and the second heat sink 18 and is in coaxial relation therewith. The lens holder 14 has an end portion received into the housing 170.

Embodiments of the present invention described above may be used in a variety of application such as, for example, processes for providing optical radiation. This includes providing the light source 52, 112 for emitting light of a predetermined wavelength at a predetermined intensity and using the first heat sink 16 or the second heat sink 18 to stabilize the temperature of the light source 52, 112. The first heat sink 16 may serve as a heat sink member having an end portion facing the recess 20. The process also includes transmitting light from the light source 52, 112 via the recess 22 and into the lens 12 portion. The first heat sink 16 conducts heat generated by the light source assembly 50, 110 into the second heat sink 18. The optical radiation from the light source 52, 112 is delivered through the lens 12 having a light entrance end 20 forming the recess 22 and is emitted through the light exit end 24 of the lens 12.

Furthermore, embodiments of the present invention also may be used to activate tooth-whitening materials. For example, to whiten teeth, a tooth whitening material is first applied to the teeth. The teeth are then exposed to the material in the absence of activating light for a substantial period of time. The material is then exposed to light having a wavelength in the range 400-600 nm. The light is generated by the light source 52, 112 portion of the illuminator assembly 10 and is emitted forwardly toward the concave wall or recess 22 defined by the lens 12 and emerges from the light exit end 24 of the lens 12. The activating light may be applied to the material at a power level of 100-600 mW for a period of 20-40 seconds, for example.

Moreover, embodiments of the present invention may be used to cure dental composite materials. For example, a dental composite material may be applied to a tooth and utilizing the light source 52, 112 comprising an array of LEDs 93, 120, 122, 124 to produce activating light having a wavelength in the range 400-600 nm, for example, the material may be cured. The light may be emitted forwardly from the light source 52, 112 toward a concave wall forming the recess 22 defined by the lens 12 at the light entrance end 20. In one embodiment of the present invention, the activating light may be applied to the dental material at a power level of 100-200 mW for a period of 2-5 seconds, for example. In another embodiment of the present invention, the dental composite material may be a resin applied to a tooth.

Although the present invention has been described with regard to certain embodiments, those of ordinary skill in the art will recognize that many modifications and variations of the present invention may be implemented. The foregoing description and the following claims are intended to cover all such modifications and variations. Furthermore, the components and processes disclosed are illustrative, but are not exhaustive. Other components and processes also may be used to make systems and methods embodying the present invention.

The invention claimed is:

1. An apparatus, comprising:
a lens having a light entrance end forming a recess defining a concave surface, wherein the lens is a non-imaging lens or a total internal reflection lens (TIR) configured to radiate optical radiation received at the concave surface;
a lens holder extending about the concave surface of the recess to receive the light entrance end of the lens;
a heat sink having an end portion facing the recess; and
a light source positioned to transmit light having a predetermined wavelength via the concave surface of the recess into the lens;
wherein the light source is in thermal communication with the heat sink to conduct heat generated by the light source to the heat sink; and
wherein the lens holder defines an inner wall that tapers in a direction toward the heat sink, the lens defining an outer surface that also tapers toward the heat sink and extends about the concave surface of the recess and in adjacent relation to the lens holder inner wall.

2. An apparatus, comprising:
a lens having a light entrance end forming a recess defining a concave surface, the lens being a non-imaging lens or a total internal reflection (TIR) lens configured to radiate collimated optical radiation therethrough, the lens further comprising a rearward portion extending about the lens recess and defining an outer surface tapering to a smaller diameter; and
a lens holder comprising a front portion extending about the lens recess, the front portion defining a first cavity for receiving the light entrance end of the lens, and a rear portion defining a second cavity to receive the end portion of a heat sink therein, the lens holder defining an inner wall therein tapering to a smaller diameter in a direction from the front portion of the lens holder to the rear portion of the lens holder;
wherein the tapered outer surface of the lens further extends into the rear portion of the lens holder and the tapered outer surface of the lens is oriented in adjacent relation to the tapered inner wall of the lens holder.

3. The apparatus of claim 2, further comprising:
a light source facing the light entrance end of the lens to transmit light having a predetermined wavelength via the lens recess into the lens.

4. The apparatus of claim 3, wherein the light source comprises an LED.

5. The apparatus of claim 3, further comprising an annular interface board located on an end portion of a heat sink to receive the light source in a central aperture defined by the annular interface board.

6. The apparatus of claim 5, wherein the light source forms an electrical contact with the heat sink.

7. The apparatus of claim 3, wherein the light source is configured to emit light having a predetermined visible wavelength forwardly toward the lens recess.

8. The apparatus of claim 3, wherein the lens recess is re-entrant into the lens and the lens includes a rearward wall that is concave toward the lens recess.

9. The apparatus of claim 3, wherein the lens recess contains at least one of the following:
 i) a curable optical plastic material having an index of refraction substantially the same as that of the lens; or
 ii) a light transmitting plastic material.

10. The apparatus of claim 3, further comprising wiring extending between the lens holder and a heat sink to supply electrical current to the light source which comprises at least one LED.

11. The apparatus of claim 3, wherein the lens includes a forward cylindrical portion extending from the rearward portion of the lens to a light exit end of the lens.

12. The apparatus of claim 3, further comprising a housing extending about the lens holder heat sink in coaxial relation therewith and the lens holder having an end portion received into the housing.

13. The apparatus of claim 3, further comprising a heat sink having an end facing the lens recess, wherein the heat sink comprises a metallic primary heat sink and a metallic secondary heat sink at an end of the primary heat sink opposite the concave surface of the recess.

14. An apparatus, comprising:
 a lens having a light entrance end forming a recess defining a concave surface, the lens being a non-imaging lens or a total internal reflection (TIR) lens configured to radiate collimated optical radiation therethrough, the lens further comprising a rearward portion extending about the lens recess and defining an outer surface tapering to a smaller diameter; and
 a lens holder comprising a front portion extending about the lens recess, the front portion defining a first cavity for receiving the light entrance end of the lens, and a rear portion defining a second cavity to receive the end portion of a heat sink therein, the lens holder defining an inner wall therein tapering to a smaller diameter in a direction from the front portion of the lens holder to the rear portion of the lens holder;
 wherein the tapered outer surface of the lens further extends into the rear portion of the lens holder and the tapered outer surface of the lens is oriented in adjacent relation to the tapered inner wall of the lens holder;
 a light source facing the light entrance end of the lens to transmit light having a predetermined wavelength via the lens recess into the lens;
 an annular interface board located on an end portion of a heat sink to receive the light source in a central aperture defined by the annular interface board; and
 a metallic film formed on the interface board, wherein the light source is electrically connected to the metallic film formed on the interface board.

15. The apparatus of claim 14, wherein the light source comprises an LED.

16. The apparatus of claim 14, wherein the light source forms an electrical contact with the heat sink.

17. The apparatus of claim 14, wherein the light source is configured to emit light having a predetermined visible wavelength forwardly toward the lens recess.

18. The apparatus of claim 14, wherein the lens recess is re-entrant into the lens and the lens includes a rearward wall that is concave toward the lens recess.

19. The apparatus of claim 14, wherein the lens recess contains at least one of the following:
 i) a curable optical plastic material having an index of refraction substantially the same as that of the lens; or
 ii) a light transmitting plastic material.

20. The apparatus of claim 14, further comprising wiring extending between the lens holder and a heat sink to supply electrical current to the light source which comprises at least one LED.

21. The apparatus of claim 14, wherein the lens includes a forward cylindrical portion extending from the rearward portion of the lens to a light exit end of the lens.

22. The apparatus of claim 14, further comprising a housing extending about the lens holder heat sink in coaxial relation therewith and the lens holder having an end portion received into the housing.

23. The apparatus of claim 14, further comprising a heat sink having an end facing the lens recess, wherein the heat sink comprises a metallic primary heat sink; and a metallic secondary heat sink at an end of the primary heat sink opposite the concave surface of the recess.

24. An apparatus, comprising:
 a lens having a light entrance end forming a recess defining a concave surface, the lens being a non-imaging lens or a total internal reflection (TIR) lens configured to radiate collimated optical radiation therethrough, the lens further comprising a rearward portion extending about the lens recess and defining an outer surface tapering to a smaller diameter; and
 a lens holder comprising a front portion extending about the lens recess, the front portion defining a first cavity for receiving the light entrance end of the lens, and a rear portion defining a second cavity to receive the end portion of a heat sink therein, the lens holder defining an inner wall therein tapering to a smaller diameter in a direction from the front portion of the lens holder to the rear portion of the lens holder;
 wherein the tapered outer surface of the lens further extends into the rear portion of the lens holder and the tapered outer surface of the lens is oriented in adjacent relation to the tapered inner wall of the lens holder;
 a light source facing the light entrance end of the lens to transmit light having a predetermined wavelength via the lens recess into the lens; and
 an annular interface board located on an end portion of a heat sink to receive the light source in a central aperture defined by the annular interface board;
 wherein the interface board comprises at least one conductive pad formed on a surface thereof, and wherein electrical current is supplied to the light source through the interface board via the conductive pad.

25. The apparatus of claim 24, wherein the interface board comprises a plurality of conductive pads formed on a surface thereof.

26. The apparatus of claim 24, wherein the interface board comprises three conductive pads spaced 120° apart.

27. The apparatus of claim 24, wherein the light source comprises an LED.

28. The apparatus of claim 24, wherein the light source forms an electrical contact with the heat sink.

29. The apparatus of claim 24, wherein the light source is configured to emit light having a predetermined visible wavelength forwardly toward the lens recess.

30. The apparatus of claim 24, wherein the lens recess is re-entrant into the lens and the lens includes a rearward wall that is concave toward the lens recess.

31. The apparatus of claim 24, wherein the lens recess contains at least one of the following:
   i) a curable optical plastic material having an index of refraction substantially the same as that of the lens; or
   ii) a light transmitting plastic material.

32. The apparatus of claim 24, further comprising wiring extending between the lens holder and a heat sink to supply electrical current to the light source which comprises at least one LED.

33. The apparatus of claim 24, wherein the lens includes a forward cylindrical portion extending from the rearward portion of the lens to a light exit end of the lens.

34. The apparatus of claim 24, further comprising a housing extending about the lens holder heat sink in coaxial relation therewith and the lens holder having an end portion received into the housing.

35. The apparatus of claim 24, further comprising a heat sink having an end facing the lens recess, wherein the heat sink comprises a metallic primary heat sink; and a metallic secondary heat sink at an end of the primary heat sink opposite the concave surface of the recess.

\* \* \* \* \*